United States Patent [19]

Terashima

[11] Patent Number: 4,865,698
[45] Date of Patent: Sep. 12, 1989

[54] REFERENCE SOLUTION FOR MEASURING IONIC ACTIVITY

[75] Inventor: Masaaki Terashima, Saitama, Japan

[73] Assignee: Fuji Photo Film Co., Ltd., Kanagawa, Japan

[21] Appl. No.: 26,920

[22] Filed: Mar. 17, 1987

[30] Foreign Application Priority Data

Mar. 17, 1986 [JP] Japan .................................. 61-58765
Apr. 18, 1986 [JP] Japan .................................. 61-89348

[51] Int. Cl.⁴ ............................................ G01N 27/46
[52] U.S. Cl. .................................... 204/1 T; 204/403; 204/416; 252/408.1
[58] Field of Search ....................... 204/416, 403, 1 T; 568/774; 429/198, 199; 252/408.1

[56] References Cited

U.S. PATENT DOCUMENTS

| | | | |
|---|---|---|---|
| 4,163,734 | 8/1989 | Sorensen et al. | 252/408 |
| 4,279,653 | 7/1981 | Makishima | 106/22 |
| 4,299,728 | 11/1981 | Cormier et al. | 252/408 |
| 4,369,127 | 1/1983 | Cormier et al. | 436/111 |
| 4,490,462 | 12/1984 | Kawaguchi | 430/543 |

*Primary Examiner*—John F. Niebling
*Assistant Examiner*—Ben C. Hsing
*Attorney, Agent, or Firm*—Sughrue, Mion, Zinn, Macpeak & Seas

[57] ABSTRACT

A reference solution for measuring an ionic activity which is utilized at the time of measuring the activity of a particular ion in an aqueous solution by the differential method using ion-selective electrodes, which is characterized by containing the compound having the general formula (I), (II) or (III) and an electrolyte.

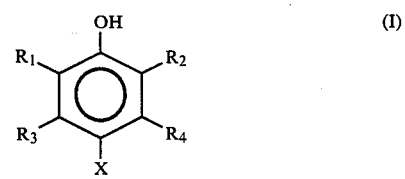

wherein $R_1$, $R_2$, $R_3$ and $R_4$ represent hydrogen atom or a lower alkyl group, respectively, and at least, one of $R_3$ and $R_4$ is a lower alkyl group, and X represents chlorine atom or bromine atom,

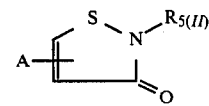

wherein $R_5$ represents hydrogen atom or a lower alkyl group and A represents a hydrogen atom or a halogen atom, and

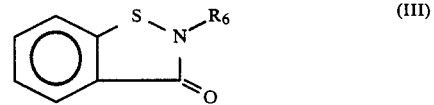

wherein $R_6$ represents a hydrogne atom or a lower alkyl group.

The reference solution of the invention may be preserved for a long period at room temperature without putrifaction, and the compound (I), (II) or (III) in the reference solution does not or scarcely influence upon the potential difference generated in the ion-selective electrode.

8 Claims, 1 Drawing Sheet

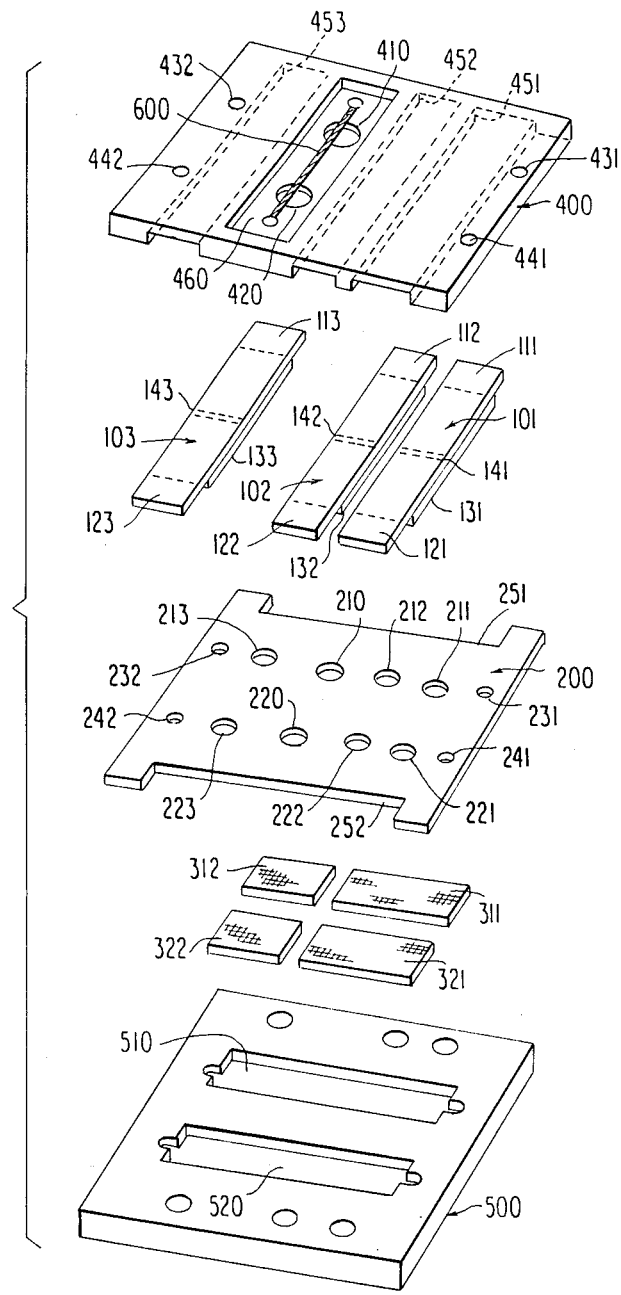

REFERENCE SOLUTION FOR MEASURING IONIC ACTIVITY

BACKGROUND OF THE INVENTION

1. Field of the Invention

This invention relates to a reference solution utilized at the time of measuring the activity of a particular ion in an aqueous solution, particularly a biological body fluid such as blood, which is superior in prevention of putrefaction.

2. Background of the Invention

When activity of a particular ion in an aqueous solution, especially in a biological body fluid such as blood is measured by the differential method using a ion-selective electrodes, a reference solution is usually employed. This reference solution is generally composed of an electrolyte such as sodium chloride, ammonium chloride, ammonium nitrate, potassium chloride, sodium hydrogen carbonate, sodium dihydrogen phosphate or potassium dihydrogen phosphate, a buffering agent, a water-soluble polymer, an antiseptic, etc. The antiseptic is added in order to prevent generation of fungi and putrefaction of the reference solution, and salicylic acid, thymol, benzoic acid, sodium azide or the like has been employed as the antiseptic. However, heretofore, even in the presence of such an antiseptic, fungi were often generated in a relatively short preservation period, and they putrefied the reference solution. Besides, the potential (difference) generated in an ion-selective electrode was often influenced by the antiseptic added.

SUMMARY OF THE INVENTION

An object of the invention is to provide a reference solution utilized at the time of measuring the activity of a particular ion in an aqueous solution by the differential method using ion-selective electrodes, in which fungi do not breed and of which putrefaction does not occur.

Another object of the invention is to provide the aforementioned reference solution in which the antiseptic does not influence the potential (difference) generated in the ion-selective electrode.

Still another object of the invention is to provide the aforementioned reference solution utilized for measuring a particular ionic activity in a biological body fluid such as blood, of which reference solution putrefaction does not occur and in which the antiseptic does not influence the potential (difference) generated in the ion-selective electrode.

Such objects can be achieved by a reference solution for measuring an ionic activity which is utilized at the time of measuring the activity of a particular ion in an aqueous solution by the differential method using ion-selective electrodes, which is characterized by containing the compound having the general formula (I), (II) or (III) described later and an electrolyte.

BRIEF DESCRIPTION OF THE DRAWING

FIG. 1 is an exploded perspective view illustrating structure of the ionic activity measuring instrument employed in the examples.

DETAILED DESCRIPTION OF THE INVENTION

The first compounds usable as the antiseptic for the reference solution of the invention are represented by the following formula (I),

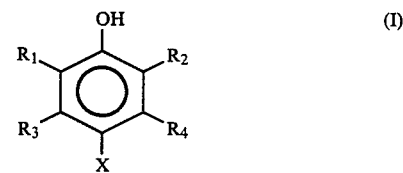

wherein $R_1$, $R_2$, $R_3$ and $R_4$ represent a hydrogen atom or a lower alkyl group, respectively, and at least, one of $R_3$ and $R_4$ is a lower alkyl group, and X represents a chlorine atom or a bromine atom.

The number of carbon atoms of every lower alkyl group is 1 to 4, and methyl group is preferable. The lower alkyl groups of $R_1$, $R_2$, $R_3$ and $R_4$ may be different from or identical with each other.

Examples of the compound (I) are 3,5-dimethyl-4-chlorophenol, 3-methyl-4-chlorophenol, 3,5-diethyl-4-chlorophenol and 2,3,5-trimethyl-4-chlorophenol.

The second compounds usable as the antiseptic for the reference solution of the invention are represented by the following formula (II),

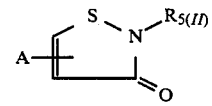

wherein $R_5$ represents a hydrggen atom or a lower alkyl group and A represents a hydrogen atom or a halogen atom.

The number of carbon atoms of the lower alkyl group is 1 to 4, and methyl group is preferable. The halogen atom includes chlorine atom, bromine atom, iodine atom and fluorine atom, and chlorine atom is preferable.

Examples of the compound (II) are 2-methylisothiazolone and 5-chloro-2-methylisothiazolone.

The third compounds usable as the antiseptic for the reference solution of the invention are represented by the following formula (III),

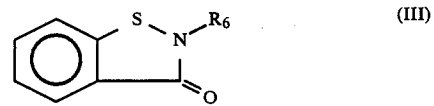

wherein $R_6$ represents a hydrogen atom or a lower alkyl group.

The number of carbon atoms of the lower alkyl group is 1 to 4, and methyl group is preferable.

Examples of the compound (III) are benzoisothiazolone and 2-methylbenzoisothiazolone.

Among them, the compound (II) is the most preferable, and the compound (I) is in the second place. The antiseptic employed may be a single material selected from the compounds (I), (II) and (III), or may be a mixture thereof. Suitable concentration in the reference solution is in the range of about 10 mg/l to about 500 mg/l, preferably about 50 mg/l to about 300 mg/l in the case of the compound (I), while it is in the range of about 3 mg/l to about 500 mg/l, desirably about 5 mg/l to about 100 mg/l in the cases of the compounds (II) and (III). The compounds (I), (II) and (III) may be dissolved with a suitable solvent such as water, ethanol, acetone, etc., and added to the reference solution.

The electrolyte contained in the reference solution may be usual one such as sodium chloride, ammonium chloride, ammonium nitrate and potassium chloride, but lithium acetate etc. are also usable. The electrolyte may be either a single material or a mixture. Suitable concentration in the reference solution is in the range of about 0.05M to about 3M. In the case of lower than 1M, the effect of the invention remarkably appears.

Other components of the reference solution of the invention may be usual, and they may be selected according to its use. For example, it is utilized for measuring a particular ionic activity in a biological body fluid such as blood, the reference solution usually further contains a buffering agent and a water-soluble polymer.

As the buffering agent, sodium hydrogen carbonate, sodium dihydrogen phosphate, potassium dihydrogen phosphate, phosphate buffer solutions containing or not containing these phosphates, Tris buffer solutions such as Tris-HCl, Tris-acetate, Tris-borate and Tris-maleate, acetate, and Good's buffer solutions described in Biochemistry Vol. 5, No.2, pp 467 to 477, such as MOPSO, MOPS, BES, TES and HEPES are usable.

As the water-soluble polymer, polyvinyl alcohol (PVA), polyvinyl pyrrolidone (PVP), polyacrylamide, serum albumin such as human serum albumin (HSA) and bovine serum albumin (BSA) are usable. Suitable content of the polymer in the reference solution is about 1 wt.% to about 15 wt.%.

Still other components may be added. For example, a coloring material such as blue or green alizarin dye may be added in order to distinguish from the sample solution such as blood serum.

The reference solution of the invention may be preserved for a long period at room temperature without putrefaction, and the compound (I), (II) or (III) in the reference solution does not or scarcely influence upon the potential difference generated in the ion-selective electrode.

EXAMPLES

Example 1

Various reference solutions having the following composition were prepared.

| | | |
|---|---|---|
| Polyvinyl pyrrolidone (K15, Tokyo Kasei) | 30 g | |
| Glycerine | 20 g | |
| Sodium chloride | 5.84400 g | |
| Sodium hydrogen carbonate | 2.52030 g | |
| Potassium dihydrogen phosphate | 0.54436 g | |
| The antiseptic in Table 1 | The amount tabulated in Table 1 | |

Total volume was adjusted to 1 l by adding distilled water.

TABLE 1

| Reference Solution | Antiseptic | Amount (mg) |
|---|---|---|
| 1 | 3,5-Dimethyl-4-chlorophenol | 100 |
| 2 | Mixture of 2-methylisothiazolone and 5-chloro-2-methylisothiazolone (1:1) w/w | 100 |
| 3 | Benzoisothiazolone | 200 |

TABLE 1-continued

| Reference Solution | Antiseptic | Amount (mg) |
|---|---|---|
| 4 | 2,4,5-Trichlorophenol | 100 |
| 5 | 4,4'-Dihydroxydiphenyl | 100 |
| 6 | Dehydroacetic acid | 500 |
| 7 | Salicylic acid | 200 |
| 8 | Benzoic acid | 200 |
| 9 | Methyl p-hydroxybenzoate | 200 |

Example 2

Each 5 ml of the above reference solutions prepared in Example 1 was palced in a vial, and 0.1 ml of 5% Malt Extract (DIFCO Co.) and 5 or 6 colonies of the fungi generated in the same reference solution not containing an antisptic were added. Then, each reference solution was allowed to stand for two weeks at room temperature, and growth of molds and bacteria after two weeks were observed. The results are shown in Table 2. In the table, + + represents abundant growth, + represents moderate growth, ± represents poor growth and — represents no growth, respectively.

TABLE 2

| Reference Solution | Molds | Bacteria |
|---|---|---|
| 1 | — | — |
| 2 | — | — |
| 3 | ± | ± |
| 4 | — | — |
| 5 | ++ | ± |
| 6 | ++ | + |
| 7 | + | + |
| 8 | + | + |
| 9 | ± | ± |

Example 3

(1) Preparation of Ag/AgCl Electrode

A continuous silver-metallized membrane 5000 Å in thickness was formed on a polyethylene terephthalate (PET) film being 180 μm thick, and cut in pieces being 28 mm in width. A score 70 μm deep was made in the center of this film in the cross direction by using the point of a knife. A mixed solvent, toluene-methyl ethyl ketone, solution of copolymer of vinyl chloride-vinyl acetate (a liquid resist for a separable coat-forming type mask) was applied on both ends of each piece in a width of 3 mm, and dried to form a protective coat 30 μm thick. This piece was immersed in an oxidative halogenation-treating solution containing 60 mM of hydrochloric acid and 12 mM of dichromic acid at 30° C. for 90 seconds, and then washed with water. This piece was dried to obtain a solid-state Ag/AgCl electrode.

(2) Preparation of Sodium Ion-Selective Electrode

A NaCl solution was applied on the above Ag/AgCl electrode in a concentration of 2 g/m² as NaCl, and then the following solution was applied thereon so that the dry coat thickness became 25 μm.

| | |
|---|---|
| Copolymer of vinyl chloride-vinyl acetate ("VYNS", Union Carbide, Polymerization ratio = 90:10) | 0.9 g |
| Dioctyl phthalate | 2.4 g |
| Methyl monensin | 0.22 g |
| Methyl ethyl ketone (MEK) | 5.0 g |

Subsequently, the resist layers coated on both ends were slowly peeled off to expose connecting terminal portions composed of silver-metallized face. This piece was cut in pieces being 6 mm in width to obtain sodium ion-selective electrode.

(3) Preparation of Potassium Ion-Selective Electrode

A mixture solution containing KCl and NaCl in an equal amount was applied on the above Ag/AgCl electrode in concentration of 1 g/m² of KCl and NaCl. Then, the following solution was applied thereon so that the dry coat thickness became 30 μm, and the resist layers of both ends were peeled off. This piece was cut in pieces being 6 mm in width to obtain potassium ion-selective electrode.

| "VYNS" | 0.9 g |
|---|---|
| Dioctyl phthalate | 2.4 g |
| Valinomycin | 44 mg |
| MEK | 5.0 g |

(4) Preparation of Chloride Ion-Selective Electrode

The following solution to form a chloride ion-selective layer was applied on the Ag/AgCl electrode described previously so that the dry coat thickness became 28 μm, and the resist layers of both ends were peeled off. This piece was out in pieces being 6 mm in width to obtain chloride ion-selective electrode.

| "VYNS" | 0.9 g |
|---|---|
| Trioctylmethylammonium chloride | 1.35 g |
| Didodecyl phthalate | 0.03 g |
| MEK | 5.0 g |

(5) Assembling of Ionic Activity Measuring Device

As illustrated in FIG. 1, the above three ion-selective electrodes 101, 102, 103 were fitted into the receiving channels 451, 452, 453 of a plastic mount 400 provided on the reverse side so that each ion-selective layer 131, 132, 133 came to the lower side. A shallow concavity 460 is formed on the left side of the center of the mount 400, and a pair of liquid supply holes 410, 420 were provided in it 460. A bridge 600 was laid across the holes 410, 420. The above channels 451, 452, 453 were provided in parallel with the concavity 460, one 453 was located on its left side, and the others 451, 452 were located on its right side. Each one pair of air vents 431 and 441, 432 and 442 was provided at each end of the mount 400. In the drawing, the left electrode is sodium ion-selective electrode 103, the central electrode is potassium ion-selective electrode 102, and the right electrode is chloride ion-selective electrode 101. Terminals 111, 121, 112, 122, 113, 123 were provided at each end of every electrode, and the score 131, 132, 133 described in item (1) is illustrated in the center of every electrode. Four pairs of liquid supply holes 211, 221, 212, 222, 210, 220, 213, 223 were provided to a double face adhesive tape 200. One pair 210, 220 was provided at the positions corresponding to the liquid supply holes 410, 420 of the mount 400, and the remaining three pairs were provided so as to supply a liquid to each ion-selective layer 141, 142, 143. Two pairs of air vents 231, 241, 232, 242 were provided to the adhesive tape 200 at the positions corresponding to the air vents 431, 441, 432, 442 of the mount 400, and recesses 251, 252 were provided at the front side and the rear side of the adhesive tape 200 so as to expose every terminal of the electrodes. This double face adhesive tape 200 was attached from the reverse side of the mount 400 to fix every electrode. Subsequently, two sets of liquid-distributing members 311, 321, 312, 322 made of long fibrous cellulose nonwoven fabric being 2.5 mm in width were attached to the adhesive tape 200 so as to cover each liquid supply hole. A support member 500 made of polyethylene having two channels 510, 520 for receiving the above liquid-distributing members 311, 321, 312, 322 was further attached to the adhesive tape 200 to form a triple ionic activity measuring device.

(6) Measurement of Electric Potential

By using the above ionic activity measuring device, the electric potential was measured as to the reference solutions described in Table 1. The terminals of each electrode were connected with an ion analyzer ("Orion Microprocessor Ion Analyzer Model 901", Orion Co.). Each reference solution was spotted to the liquid supply hole 410, and simultaneously, a reference solution having the same composition without antiseptic was spotted to the other liquid supply hole 420. The electric potential generated was measured after one minute, and tabulated in Table 3.

TABLE 3

| Reference Solution | Electric Potential (mV) | | |
|---|---|---|---|
| | Na⁺ | K⁺ | Cl⁻ |
| 1 | 0.1 | −0.3 | −0.2 |
| 2 | 0.1 | −0.8 | −0.1 |
| 3 | −0.5 | −0.2 | −0.1 |
| 4 | 0.2 | 4.1 | 0.3 |
| 5 | 0.2 | 5.5 | 0.4 |
| 6 | −0.4 | −0.2 | 1.4 |
| 7 | −0.3 | −0.1 | 1.1 |
| 8 | −0.2 | 0.3 | 0.9 |
| 9 | 1.1 | 1.5 | 0.2 |

As shown in the table, in the cases of reference solutions of the invention (Nos. 1, 2 and 3), influence of the antiseptic added upon the electric potential was minor, while in the cases of the reference solutions using conventional antiseptics, the electric potentials varied about or more than 1 mV as to one or more ion species.

I claim:

1. A reference solution for measuring the activity of sodium ions, potassium ions or chloride ions in an aqueous solution by a differential method using ion-selective electrodes, said reference solution comprising (a) at least one compound having the general formula (I)

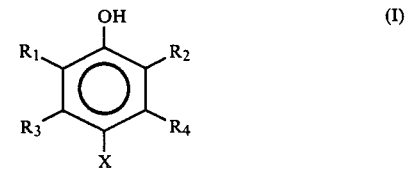

wherein $R_1$, $R_2$, $R_3$ and $R_4$ represent a hydrogen atom or a lower alkyl group, respectively, and at least one of $R_3$ and $R_4$ is a lower alkyl group, and X represents a chlorine atom or a bromine atom and (b) at least one electrolyte selected from the group consisting of sodium chloride, ammonium chloride, ammonium nitrite, potassium chloride and lithium acetate.

2. The reference solution of claim 1, wherein said lower alkyl group is methyl group or ethyl group and said X represents a chlorine atom.

3. The reference solution of claim 2, wherein said compound is selected from the group consisting of 3,5-dimethyl-4-chlorophenol, 3-methyl-4-chloropheno, 3,5-diethyl-4-chlorophenol and 2,3,5-trimethyl-4-chlorophenol.

4. The reference solution of claim 1, wherein concentration of said compound is in the range of 10 mg/l to 500 mg/l.

5. The reference solution of claim 1, wherein concentration of said electrolyte is 0.05M to 1M.

6. The reference solution of 1, which further contains a buffering agent and a water-soluble polymer.

7. The reference solution of claim 1, wherein said aqueous solution is a sample of a biological body fluid.

8. a method for measuring activity of sodium ions, potassium ions or chloride ions in an aqueous solution by the differential method using ion-selective electrodes and a reference solution comprising adding to said reference solution (a) at least one compound having the general formula (I)

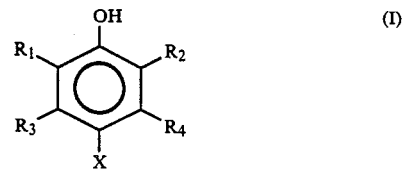

wherein $R_1$, $R_2$, $R_3$, and $R_4$ represent a hydrogen atom or a lower alkyl group, respectively, and at least one of $R_3$ and $R_4$ is a lower alkyl group, and X represents a chlorine atom or a bromine atom and (b) at least one electrolyte selected from the group consisting of sodium chloride, ammonium chloride, ammonium nitrite, potassium chloride and lithium acetate.

* * * * *